US006904122B2

(12) United States Patent
Swift et al.

(10) Patent No.: US 6,904,122 B2
(45) Date of Patent: Jun. 7, 2005

(54) 3D STEREOSCOPIC X-RAY SYSTEM

(75) Inventors: David C. Swift, Cortlandt Manor, NY (US); Sadeg M. Faris, Pleasantville, NY (US)

(73) Assignee: InventQjaya Sdn. Bhd., Cyberjaya (MY)

( * ) Notice: Subject to any disclaimer, the term of this patent is extended or adjusted under 35 U.S.C. 154(b) by 81 days.

(21) Appl. No.: 10/284,851

(22) Filed: Oct. 31, 2002

(65) Prior Publication Data

US 2003/0081720 A1 May 1, 2003

Related U.S. Application Data

(60) Provisional application No. 60/334,865, filed on Oct. 31, 2001.

(51) Int. Cl.[7] ................................................. G21K 4/00
(52) U.S. Cl. .......................................... 378/41; 378/57
(58) Field of Search .............................. 378/41, 42, 57, 378/58, 163, 164, 205, 207; 382/131, 132; 600/426

(56) References Cited

U.S. PATENT DOCUMENTS

| | | | | |
|---|---|---|---|---|
| 2,275,857 | A |   | 3/1942 | Lowitzsch ................... 250/66 |
| 5,155,750 | A |   | 10/1992 | Klynn et al. ................. 378/42 |
| 6,160,870 | A | * | 12/2000 | Jacobson ..................... 378/165 |
| 6,256,372 | B1 | * | 7/2001 | Aufrichtig et al. ............ 378/41 |
| 6,317,481 | B1 | * | 11/2001 | Berestov ...................... 378/41 |
| 6,347,131 | B1 | * | 2/2002 | Gusterson .................... 378/54 |
| 6,381,302 | B1 | * | 4/2002 | Berestov ...................... 378/41 |
| 6,584,170 | B2 | * | 6/2003 | Aust et al. .................... 378/57 |
| 6,603,481 | B1 | * | 8/2003 | Kawai et al. ................. 345/505 |
| 2004/0062346 | A1 | * | 4/2004 | Fernandez .................... 378/41 |

FOREIGN PATENT DOCUMENTS

| | | |
|---|---|---|
| DE | 19823448 A1 | 11/1999 |
| EP | 0261984 | 9/1987 |
| WO | WO99/17555 | 4/1999 |

OTHER PUBLICATIONS

"Stereoscopic Imaging Via Rotation and Translation" by M.A. Weissman of Perspective Systems, Federal Way, Washington, published on Feb. 7, 1995.

International Search Report, International Application No. PCT/US03/34999, mailed on Jun. 24, 2003; International Publication No. WO 03/039213 A3.

* cited by examiner

*Primary Examiner*—Allen C. Ho
(74) *Attorney, Agent, or Firm*—Gerow D. Brill; Ralph J. Crispino

(57) ABSTRACT

The present invention provides a means to augment or upgrade a traditional single beam 2D x-ray system to produce 3D stereoscopic output. The system utilizes the cross-sectional beam divergence of a single source x-ray unit to generate perspective information. This is achieved by scanning the object twice where the object is shifted parallel to the cross-sectional beam plane between scans. The resulting two scans can be displayed on a 3D stereoscopic viewing system to produce a 3D stereoscopic representation of the object thus revealing all three-depth dimensions. The invention includes a method of converting a 2D x-ray system to a 3D x-ray system requiring no changes to an x-ray generation portion, optics portion or sensing system portion of said 2D x-ray system. The method includes coupling a 3D stereoscopic image processor to a 2D processor and installing a mechanical shift system and coupling said shift system to said 3D stereoscopic image processor and a object carrying device.

23 Claims, 3 Drawing Sheets

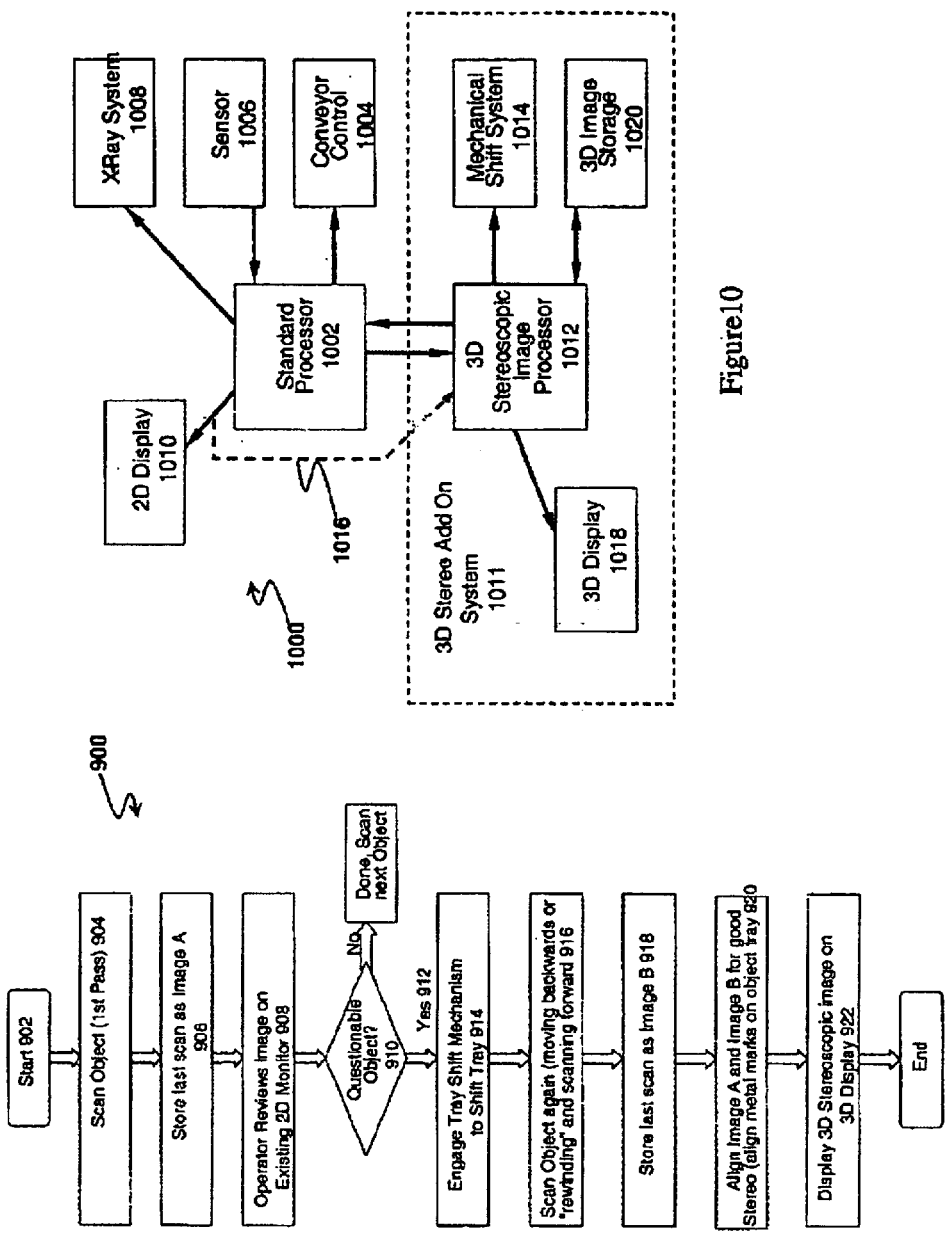

3D STEREOSCOPIC X-RAY SYSTEM

CROSS-REFERENCES

This application is related to provisional patent application 60/334,865 filed on Oct. 31, 2001 entitled 3D Stereoscopic X-ray System and Method and is hereby incorporated by reference.

FIELD OF INVENTION

The present invention is related to a stereoscopic x-ray system, in particular a stereoscopic x-ray system for baggage inspection and to a modification of existing two-dimensional x-ray inspection systems requiring no additional x-ray source.

BACKGROUND OF THE INVENTION

Traditional x-ray scanning systems use a single stationary x-ray beam (in the form of a thin expanding planar beam) to scan objects that are moved through the beam. The result is a 2D flat projection of the object indicating transmission intensity of the x-ray beams through the object. Many systems provide multiple sensitivity sensors to help discriminate the various absorption properties of the object at different x-ray powers. The 2D images produced by these systems only provide spatial information in two dimensions. The third spatial dimension, depth, is not provided by traditional systems. For applications like security and inspection, this missing third dimension can lead to lost information or misinterpreted information.

Systems have been developed to capture the third dimension using two x-ray beams. These devices have been successfully demonstrated. These two beam systems require a new configuration for the x-ray device and would require traditional single-beam devices to be replaced. The present invention does not require a reconfiguration of a traditional single-beam because it functions as a parallel system along with the existing 2D x-ray functionality.

SUMMARY OF THE INVENTION

The present invention provides a means to augment or upgrade a traditional single beam 2D x-ray system to produce 3D stereoscopic output. The system utilizes the cross-sectional beam divergence of a single source x-ray unit to generate perspective information. This is achieved by scanning the object twice where the object is shifted parallel to the cross-sectional beam plane between scans. The resulting two scans can be displayed on a 3D stereoscopic viewing system to produce a 3D stereoscopic representation of the object thus revealing all three-depth dimensions.

The invention includes a method of converting a 2D x-ray system to a 3D x-ray system requiring no changes to an x-ray generation portion, optics portion or sensing system portion of the 2D x-ray. This method includes coupling a 3D stereoscopic image processor to a 2D processor and installing a mechanical shift system and coupling the shift system to a 3D stereoscopic image processor and a object carrying device.

BRIEF SUMMARY OF THE DRAWINGS

The following drawings along with the Detailed Description are descriptive of the various embodiments of the invention wherein:

FIG. 9 is an augmented scanning process flow chart; and

FIG. 10 is a block diagram of the augmented system.

DETAILED DESCRIPTION OF THE INVENTION

Figure 2:
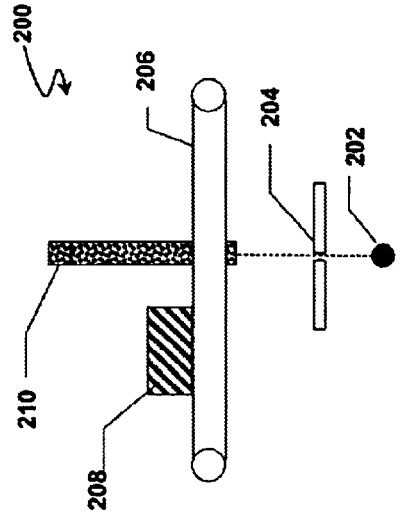
FIG. 2 illustrates a side view of a traditional X-ray system.
Figure 1:
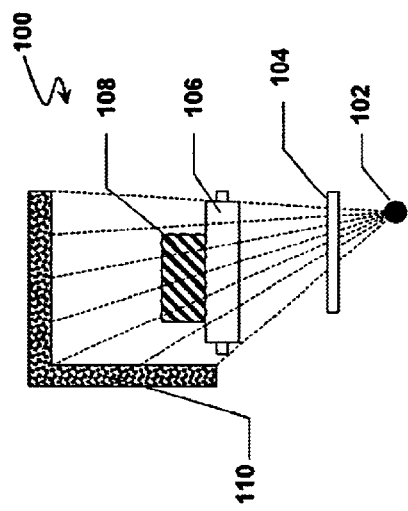
FIG. 1 illustrates a front view of a traditional X-ray system (Front View)

FIG. 1 illustrates a front view of a traditional single beam x-ray device 100. An x-ray source 102 produces x-rays that are shaped into a thin planar beam by a collimator 104. The planar beam passes through an object carrying device or conveyor belt 106 and the object to be scanned 108 and is detected by a linear x-ray sensor 110. Typical sensors respond to both high and low energy particles. The conveyor belt 106 moves the object 108 through the scanning beam. FIG. 2 illustrates a side view of a system 200 similar to that illustrated in FIG. 1 with reference numbers 202–210 representing the same elements as in FIG. 1.

Figure 3:
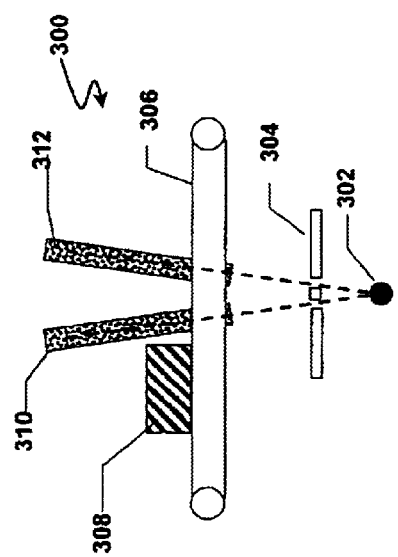
FIG. 3 illustrates an existing 3D stereoscopic X-ray solution.

FIG. 3 illustrates an existing 3D stereoscopic x-ray solution 300 where a single x-ray source 302 is collimated into two diverging planar beams by collimator 304. Each beam is directed to a different sensor 310 and 312. As the object 308 passes through both beams, two views of the object, with slightly different rotational axis, are generated. Once processed, these two views form a 3D stereoscopic image of the objects x-ray transmission/absorption characteristics. This system requires that the traditional x-ray device be modified to include two sensors, Sensor A 310 and Sensor B 312.

Figure 4:
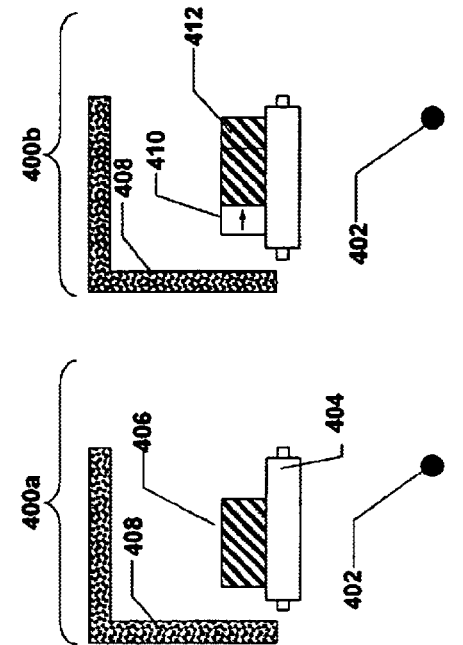
FIG. 4 illustrates a side shift method for forming a 3D stereoscopic X-ray.
Figure 5:
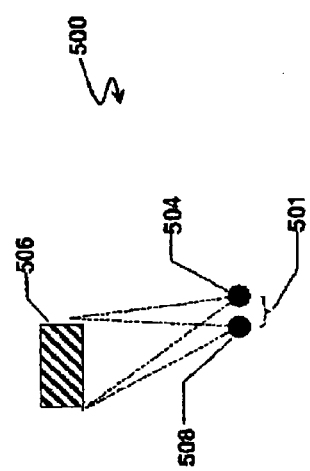
FIG. 5 illustrates a resulting stereo base using a side shift method.

The present invention provides a system to create 3D stereoscopic x-ray images and a means to augment or modify existing 2D x-ray systems to provide a 3D stereoscopic x-ray image. By scanning the object twice using a traditional x-ray device and side shifting the object slightly between scans, two images can be captured and then combined in a 3D stereoscopic image. FIG. 4 illustrates the concept of scanning an object 400a using a traditional 2D x-ray system, side-shifting the object, and then scanning the abject again 400b. The object 406 is shown in a first position in a first pass scan 400A with the x-ray source, conveyor and sensor as shown in FIGS. 1 and 2. Notice that the object 406 is shifted slightly to the right 412 front its previous object position 410 for the second scan as shown in a second pass scan 400B with the x-ray source 402, the conveyor 404 and sensor 408 unchanged. This side-shift has the effect of shifting the origin of the x-ray emitter with respect to the object. The side-shift occurs within the plane of the X-ray scanning beam. The orientation plane of the X-ray beam can be described by a vector perpendicular to the planar surface. The object is shifted perpendicular to this normal vector. If the first and second pass scans are superimposed using the same object position, it becomes apparent that a 3D stereoscopic image can be generated as shown by the system 500 in FIG. 5. The effective stereo base 501 is based on the first scan position 504 of the object 506 relative to the second scan position of the object 508. The effective stereo base is the same as the amount of side-shift between scans. The amount of side shift required is the same as the desired stereo base that can be computed using stereoscopic camera algorithms well known to one skilled in the art.

Figure 6:
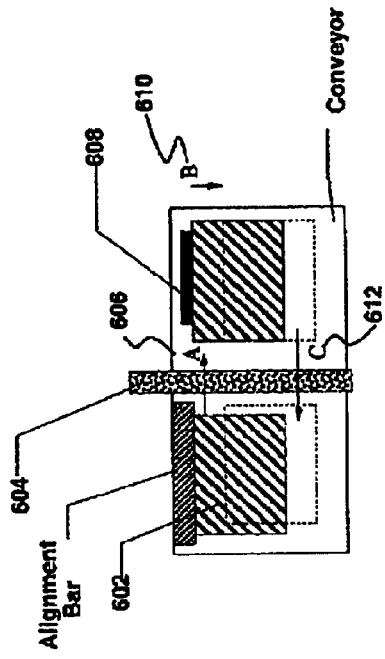
FIG. 6 illustrates a two-scan process for a side shift method.

FIG. 6 illustrates a top view of the side-shift method 600. During the first scan, the object 602 passes under the sensor 604 along trajectory A 606. After the first scan, an object shift system 608 moves the object to the right along trajectory B 610 and the conveyor belt is reversed and the object scans back through the sensor along trajectory C 612. The results of the first and second scans can be combined into a 3D stereoscopic image. The first scan generates the right perspective and the second scan generates the left perspective. The process of forming a stereoscopic image from a left and right image pair is well known in the art of 3D stereoscopic imaging.

Figure 7:
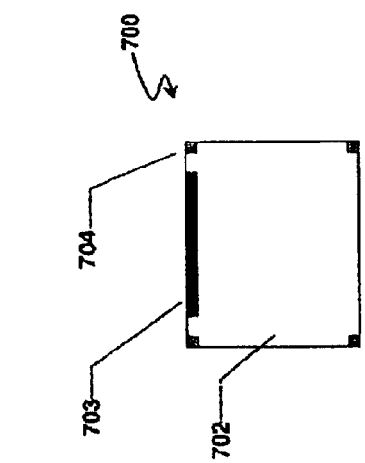
FIG. 7 illustrates an object support tray with alignment marks.

FIG. 7 illustrates an embodiment of a tray to hold the object to be scanned 700. This tray 702 (generally including a shift mechanism support 703) contains one or more metal or other dense material alignment marks 704, which will appear on the final scanned images. These alignment marks 704 are used by the 3D stereo image processor to align the right and left image pairs. The process of aligning left and right images is well known to one skilled in the art.

Figure 8:
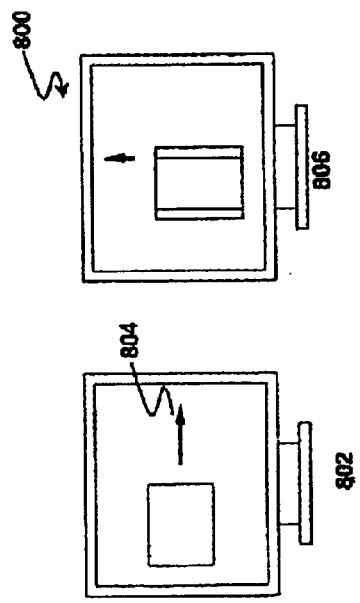
FIG. 8 illustrates an object direction of travel and a stereo base direction.

FIG. 8 illustrates the difference between the directions of travel of the object on the viewing monitor 800. A traditional x-ray system 802 will display the scanned object with the conveyor travel direction along the horizontal axis of the monitor 804. The proposed invention 806 displays the scanned object with the conveyor travel direction along the vertical axis of the monitor since the 3D stereoscopic image base is perpendicular to the direction of travel of the conveyor belt.

FIG. 9 illustrates a flowchart of a scanning process 900. The object is scanned 904 and the resulting image is stored by the 3D stereoscopic image process as image A 906. The operator optionally reviews the 2D image 908 and determines if a second scan is required 910. If a second scan is not required, the next object is scanned. This second scan decision point 910 can be skipped if 3D stereoscopic output is desired for all scans. If the object is going to be re-scanned to form a 3D image 912, the tray shift mechanism 914 is engaged to side shift the object on the conveyor 916 and the object is scanned a second time and the resulting image is stored as image B 918. Then, image A and image B are aligned in 3D (as known in the art) 920, and finally displayed on a 3D stereoscopic display device 922.

FIG. 10 illustrates a block diagram of the proposed system 1000. The five boxes; standard processor 1002, conveyor control 1004, sensor 1006, x-ray system 1008 and 2D display 1010 outside of the dashed box 1011 represent a standard x-ray processing system. The standard processor 1002 controls the conveyor system 1004 to move an object through an x-ray beam that is generated by the x-ray system 1008. The sensor 1006 converts the x-ray intensity into a digital form, which the standard processor 1002 converts into a 2D image. The 2D image is displayed on the 2D Display 1010.

The dashed box 1011 in FIG. 10 illustrates the augmented 3D stereoscopic features. The 3D stereoscopic image processor 1012, instructs the standard x-ray processor to scan the object, then enables the mechanical shift system 1014 to side shift the object, then instructs the standard processor 1002 to re-scan the object. The 3D stereoscopic image processor 1012 receives the scanned image from the standard processor or, optionally, intercepts the data before it is displayed on the 2D display (as indicated by the dashed information line 1016). The 3D stereoscopic image processor 1012 then aligns the right and left images (acquired during the two scans) and displays them on the 3D display system 1018. An optional 3D image storage system 1020 can be used to save copies of the scanned 3D x-ray images for future reference.

Another embodiment is a method of modifying a 2D X-ray system to a 3D stereoscopic system wherein the 2D system includes an X-ray source, a collimator, a conveyor system for carrying an object, a 2D processor, a sensor and 2D display. The method includes adding a 3D Stereo Add-On System. The Add-On System includes: a 3D stereoscopic image processor coupled to the 2D processor; a mechanical shift system electrically coupled to the 3D stereoscopic image processor and mechanically coupled to the object carrying device; a 3D image storage device coupled to the 3D stereoscopic image processor and a 3D display coupled to the 3D stereoscopic image processor, wherein the 3D stereo add-on system requires no changes to the X-ray generation, optics or sensing system portions of the 2D X-ray system.

An additional embodiment of the 3D stereoscopic X-ray system uses an angular change in the position of the object between scans by the system. In the first pass, the object is in a first position as it passes through the detection system and prior to the second pass the object is rotated a few degrees, 2 to 5 degrees, about the axis of the moving direction of the object. The object is passed a second in time in its rotated position. The stereoscopic effect is obtained using similar stereoscopic algorithms discussed above.

The 3D stereoscopic X-ray system described herein has a primary application for baggage and package security in the transportation industry. However other applications include medical, quality control and material inspection. The same principles can be used for large size X-ray scanners for ship cargo and truck cargo. One additional feature of a 3D stereoscopic X-ray system is that moving parts will show up as disturbances in the 3D stereoscopic image. Since the left and right images are captured at different time points, a clock mechanism or other moving device will be easy to see using 3D imaging.

The system and method of modification above are merely exemplary. It is understood that other embodiments of the system and method of modification will readily occur to persons of ordinary skill in the art. All such embodiments and modifications are deemed to be within the scope and spirit of the present invention as defined by the accompanying claims.

What is claimed is:

1. A stereoscopic x-ray system for scanning objects comprising:
   an x-ray source;
   a collimator;
   an object-carrying device configured for supporting at least one object;
   a sensor; and
   an object shift system configured and positioned to shift the object upon the object carrying device.

2. The system of claim 1 wherein said stereoscopic x-ray system performs a first scan at a first scan position, by having the object pass under said sensor along a first trajectory; said stereoscopic x-ray system moving said object to a second scan position along a second trajectory with the object shift system and; said object-carrying device is reversed and said stereoscopic x-ray system performs a second scan of the object back through said sensor along a third trajectory.

3. The system of claim 2 wherein results of said first and second scan are combined into a 3D stereoscopic image.

4. The system of claim 3 wherein said first scan generates a right perspective and said second scan generates a left perspective.

5. The system of claim 1 wherein said stereoscopic x-ray system performs a first scan, by having the object pass under said sensor along a first trajectory; said stereoscopic x-ray system rotating said object 2–5 degrees about an axis of said first trajectory with the object shift system and; said object-carrying device is reversed and said stereoscopic x-ray system performs a second scan of the object back through said sensor along a second trajectory.

6. The system of claim 5 wherein results of said first and second scan are combined into a 3D stereoscopic image.

7. The system of claim 6 wherein said first scan generates a right perspective and said second scan generates a left perspective.

8. The system of claim 1 wherein said object carrying device contains one or more metal or other dense material alignment marks.

9. The system of claim 8 wherein said alignment marks appear on the final scanned images.

10. The system of claim 9 wherein said alignment marks are used by a 3D stereo image processor to align the right and left image pairs.

11. A 3D Stereo Add-On system for modifying a 2D X-ray system to a 3D stereoscopic system wherein said 2D system comprises an X-ray source, a collimator, an object-carrying device for carrying an object, a 2D processor, a sensor and a 2D display said add-on system comprising:
  a 3D stereoscopic image processor coupled to said 2D processor;
  a mechanical shift system coupled to said 3D stereoscopic image processor and coupled to said object-carrying device;
  a 3D image storage device coupled to said 3D stereoscopic image processor and a 3D display coupled to said 3D stereoscopic image processor, wherein said 3D stereo add-on system requires no changes to the X-ray generation, optics or sensing system portions of said 2D X-ray system.

12. The system of claim 11 wherein said 3D Stereo Add-On system performs a first scan, by having the object pass under said sensor along a first trajectory and said 3D Stereo Add-On system moves said object to the right along a second trajectory with the mechanical shift system and; said object-carrying device is reversed and said 3D Stereo Add-On system performs a second scan of the object back through said sensor along a third trajectory.

13. The system of claim 12 wherein results of said first and second scan are combined into a 3D stereoscopic image.

14. The system of claim 13 wherein said first scan generates a right perspective and said second scan generates a left perspective.

15. The system of claim 11 wherein said 3D Stereo Add-On system performs a first scan, by having the object pass under said sensor along a first trajectory; and said 3D Stereo Add-On system rotates said object 2–5 degrees about an axis of said first trajectory and; said object-carrying device is reversed and said 3D Stereo Add-On system performs a second scan of the object back through said sensor along a second trajectory.

16. The system of claim 15 wherein results of said first and second scan are combined into a 3D stereoscopic image.

17. The system of claim 16 wherein said first scan generates a right perspective and said second scan generates a left perspective.

18. The system of claim 11 wherein said object carrying device contains one or more metal or other dense material alignment marks.

19. The system of claim 18 wherein said alignment marks appear on the final scanned images.

20. The system of claim 19 wherein said alignment marks are used by a 3D stereo image processor to align the right and left image pairs.

21. A method of converting a 2D x-ray system to a 3D x-ray system requiring no changes to an x-ray generation portion, optics portion or sensing system portion of said 2D x-ray system comprising:
  coupling a 3D stereoscopic image processor to a 2D processor; and
  installing a mechanical shift system and coupling said shift system to said 3D stereoscopic image processor and a object carrying device.

22. The method of claim 21 wherein a 3D image storage device is coupled to said 3D stereoscopic image processor.

23. The method of claim 21 wherein said object carrying device one or more alignment marks.

* * * * *